United States Patent
Penenberg (12) 
(10) Patent No.: US 6,997,928 B1
(45) Date of Patent: Feb. 14, 2006

(54) APPARATUS FOR AND METHOD OF PROVIDING A HIP REPLACEMENT

(75) Inventor: Brad L. Penenberg, Beverly Hills, CA (US)

(73) Assignee: Wright Medical Technology, Inc., Arlington, TN (US)

(*) Notice: Subject to any disclaimer, the term of this patent is extended or adjusted under 35 U.S.C. 154(b) by 0 days.

(21) Appl. No.: 10/932,742

(22) Filed: Sep. 1, 2004

Related U.S. Application Data (63) Continuation of application No. 10/683,008, filed on Oct. 9, 2003, now Pat. No. 6,905,502, and a continuation of application No. 10/166,209, filed on Jun. 10, 2002, now abandoned.

(51) Int. Cl.
A61B 17/56 (2006.01)

(52) U.S. Cl. .......................................... 606/81; 606/91

(58) Field of Classification Search ................ 128/898; 606/80, 81, 86, 89, 91, 99, 104; 623/22.11, 623/22.12, 22.15, 22.4, 22.21
See application file for complete search history.

(56) References Cited

U.S. PATENT DOCUMENTS

| | | |
|---|---|---|
| 3,685,058 A | 8/1972 | Tronzo |
| 3,859,992 A | 1/1975 | Amstutz |
| 3,874,003 A | 4/1975 | Moser et al. |
| 4,305,394 A | 12/1981 | Bertuch, Jr. |
| 4,399,813 A | 8/1983 | Barber |
| 4,475,549 A | 10/1984 | Oh |
| 4,528,980 A | 7/1985 | Kenna |
| 4,632,111 A | 12/1986 | Roche |
| 4,662,891 A | 5/1987 | Noiles |
| 4,677,972 A | 7/1987 | Tornier |
| 4,716,894 A | 1/1988 | Lazzeri et al. |
| 4,865,025 A * | 9/1989 | Buzzi et al. ................... 606/96 |
| 4,878,918 A | 11/1989 | Tari et al. |
| 4,994,064 A | 2/1991 | Aboczsky |
| 5,030,221 A | 7/1991 | Buechel et al. |
| 5,037,424 A | 8/1991 | Aboczsky |
| 5,061,270 A | 10/1991 | Aboczsky |
| 5,098,437 A | 3/1992 | Kashuba et al. |
| 5,108,448 A | 4/1992 | Gautier |

(Continued)

FOREIGN PATENT DOCUMENTS

EP 0147339 A2 7/1985

(Continued)

OTHER PUBLICATIONS

Murphy, Minimally invasive Hip Surgery, From www.stephenmurphy.org (2003).

(Continued)

*Primary Examiner*—Eduardo C. Robert
*Assistant Examiner*—David Comstock (57) ABSTRACT

A short main incision and portal incisions at portal positions strategically displaced from the main incision are provided in a patient's hip. One portal incision (acetabular portal) provides for a disposition of reamers in the patient's acetabulum to shape the acetabulum. A cannula is inserted through the portal incision to the acetabulum and the successive reamers of progressive size are inserted into the acetabulum through the main incision to progressively size and shape the acetabulum. An approximately hemispherical acetabular component is then disposed in the prepared acetabulum to provide for hip rotation relative to the femoral component. The other portal incision (femoral portal) provides for insertion into the patient's hip of a member for driving the femoral stem into a cavity in the patient's femur. The provision of the short main incision and the portal incision minimizes the patient's loss of blood, tissue trauma, length of operating time and patient recovery time.

43 Claims, 6 Drawing Sheets

U.S. PATENT DOCUMENTS

| | | | |
|---|---|---|---|
| 5,108,452 | A | 4/1992 | DeMane et al. |
| 5,116,339 | A | 5/1992 | Glock |
| D331,461 | S | 12/1992 | Lester |
| 5,169,399 | A | 12/1992 | Ryland et al. |
| 5,171,243 | A | 12/1992 | Kashuba et al. |
| 5,171,313 | A | 12/1992 | Salyer |
| 5,190,422 | A | 3/1993 | Lechot |
| 5,217,499 | A | 6/1993 | Shelley |
| 5,250,051 | A | 10/1993 | Maryan |
| 5,261,915 | A | 11/1993 | Durlacher et al. |
| 5,284,483 | A | 2/1994 | Johnson et al. |
| 5,320,625 | A | 6/1994 | Bertin |
| 5,344,461 | A | 9/1994 | Philpot |
| 5,364,403 | A | 11/1994 | Petersent et al. |
| 5,417,696 | A | 5/1995 | Kashuba et al. |
| 5,458,637 | A | 10/1995 | Hayes |
| 5,474,560 | A * | 12/1995 | Rohr, Jr. ............ 606/91 |
| 5,486,181 | A | 1/1996 | Cohen et al. |
| 5,499,985 | A | 3/1996 | Hein et al. |
| 5,507,748 | A | 4/1996 | Sheehan et al. |
| 5,658,290 | A | 8/1997 | Lechot |
| 5,683,399 | A | 11/1997 | Jones |
| 5,814,050 | A * | 9/1998 | Benson ............ 606/102 |
| 5,891,158 | A | 4/1999 | Manwaring et al. |
| 5,904,688 | A | 5/1999 | Gilbert |
| 5,928,287 | A | 7/1999 | Keller |
| 5,968,049 | A | 10/1999 | DaRold |
| 6,063,123 | A | 5/2000 | Burrows et al. |
| 6,063,124 | A | 5/2000 | Amstutz |
| 6,106,536 | A | 8/2000 | Lechot |
| 6,129,732 | A | 10/2000 | Lechot |
| 6,132,469 | A | 10/2000 | Schroeder |
| 6,254,604 | B1 | 7/2001 | Howell |
| 6,254,605 | B1 * | 7/2001 | Howell ............ 606/96 |
| 6,264,647 | B1 | 7/2001 | Lechot |
| 6,371,124 | B1 | 4/2002 | Whelan |
| 6,482,209 | B1 | 11/2002 | Engh et al. |
| 6,626,913 | B1 | 9/2003 | McKinnon et al. |
| 6,676,706 | B1 | 1/2004 | Mears |
| 2001/0006593 | A1 | 7/2001 | Lechot |
| 2002/0002365 | A1 | 1/2002 | Lechot |
| 2002/0010470 | A1 | 1/2002 | Lechot |
| 2002/0099447 | A1 | 7/2002 | Mears et al. |
| 2002/0116067 | A1 | 8/2002 | Mears et al. |
| 2002/0193797 | A1 | 12/2002 | Johnson et al. |
| 2003/0004513 | A1 | 1/2003 | Guzman et al. |
| 2003/0050645 | A1 | 3/2003 | Parker et al. |
| 2003/0097135 | A1 | 5/2003 | Penenberg |
| 2003/0158559 | A1 * | 8/2003 | Diaz ............ 606/91 |
| 2003/0181916 | A1 | 9/2003 | Wolford |
| 2003/0220696 | A1 | 11/2003 | Mears et al. |
| 2003/0229352 | A1 | 12/2003 | Penenberg |
| 2003/0229356 | A1 | 12/2003 | Dye |
| 2003/0229357 | A1 | 12/2003 | Dye |

FOREIGN PATENT DOCUMENTS

| | | |
|---|---|---|
| EP | 0357270 A1 | 3/1990 |
| EP | 0470912 A2 | 2/1992 |
| EP | 1149562 A2 | 10/2002 |
| EP | 1149562 A3 | 1/2003 |
| GB | 2372707 A | 9/2002 |
| WO | WO03/057049 A1 | 7/2003 |
| WO | WO03/065906 A2 | 8/2003 |

OTHER PUBLICATIONS

Author unknown, Short External Rotator Muscles of the Hip. From www.biyee.net/running/injury/short_rotators.html (2002).

Precimed tool advertisement (2002).

Minimally Invasive Hip Surgery and Future Developments, From www.essexhipsurgeon.co.uk/minimally_invasive_hip_replacement_surgery.html (2003).

Innomend MIS catalog (2003).

McTighe, A New Era of Minimally Invasive Surgical Approaches for THA, Joint Implant Surgery & Research Foundation Update (Dec., 2002).

Berry, et al. Symposium on Minimally Invasive THA, J. Bone Joint Surg. 85A: 2235-2246 (2003).

Pellegrini, et al., Surgical Approaches to the Hip Joint. In: Surgery of the Musculoskeletal System (C. M. Evarts, Ed.), Churchill Livingstone (New York, NY) Chapter 94, pp. 2735-2756 (1990).

Murphy, Alumina Ceramic-Ceramic Total Hip Arthroplasty Using Computer-Assisted Surgical Navigation and a New Minimally Invasive Technique. In: Bioceramics in Joint Arthroplasty (2004).

* cited by examiner

APPARATUS FOR AND METHOD OF PROVIDING A HIP REPLACEMENT

CROSS REFERENCE TO RELATED APPLICATIONS

This application is a continuation of and claims priority to application Ser. No. 10/683,008, filed Oct. 9, 2003, now U.S. Pat. No. 6,905,502, and application Ser. No. 10/166,209, filed Jun. 10, 2002 (the parent of application Ser. No. 10/683,008), which is abandoned, the entire disclosures of which are incorporated herein by reference.

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

This invention relates to a method of providing a replacement for a patient's hip with a minimal loss of blood, minimal tissue trauma and a minimal length of operating time and patient recovery time. The invention also relates to a tool which is needed in the method constituting this invention.

BACKGROUND OF A PREFERRED EMBODIMENT OF THE INVENTION

Great progress has been made in the field of hip replacements. Considering that hip replacements may not even have existed a generation ago, hip replacements, particularly among the elderly, are now relatively common. In spite of the considerable progress which has been made, hip replacement operations are still relatively crude. For example, an incision of a relatively great length still has to be made in a patient's hip as one of the first steps in a hip replacement operation. The incision may be as long as approximately eight inches (8") to approximately twelve inches (12"). Such a large incision has caused patients to lose large amounts of blood and to suffer significant trauma. It has caused the length of the operation and the patient recovery time to be relatively long.

BRIEF DESCRIPTION OF A PREFERRED EMBODIMENT OF THE INVENTION

A minimal length main incision (e.g., approximately 1½"–3" long) and two portal incisions (each significantly less than 1" long) strategically displaced from the main incisions are provided in a patient's hip. A cannula is inserted through the portal incision to the acetabulum and a shaft is inserted through the cannula. A reamer is disposed through the main incision in the acetabulum and coupled to the shaft to ream the acetabulum when the shaft is rotated. Reamers of progressive size are then coupled to the shaft to progressively shape and size a socket in the acetabulum. An approximately hemispherical acetabular component is then disposed in the acetabulum to provide for hip rotation relative to the femur. The other portal (femoral portal) incision provides for a preparation of an insertion of a member into the patient's hip for preparing a femoral canal and then driving the femoral stem into a cavity in the patient's femur.

The provision of the main incision and the portal incisions minimizes the patient's loss of blood, tissue trauma, length of operating time and patient recovery time.

DETAILED DESCRIPTION OF A PREFERRED EMBODIMENT OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
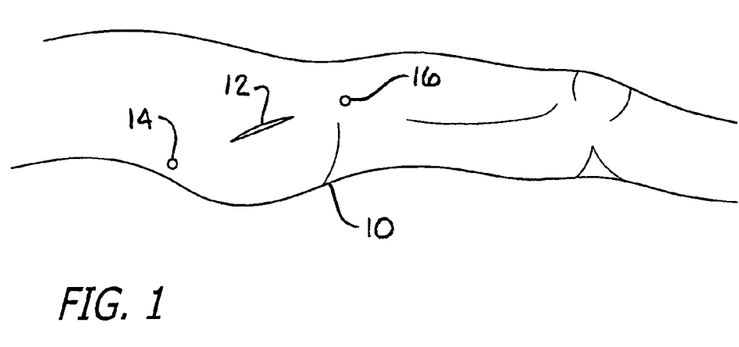
FIG. 1 is a fragmentary schematic side elevational view of a patient's hip and shows a main incision and portal incisions made in the patient's hip as an initial step in providing for a replacement of the patient's hip.

FIGS. 1–15 show progressive steps in performing a method constituting a preferred embodiment of the invention and also show apparatus included in the patentable features of the preferred embodiment of this invention. FIG. 1 schematically shows a patients hip 10 and also shows a main incision 12 and a pair of portal incisions 14 and 16. The main incision 12 may be as short as approximately one inch (1") long. The incision 16 may be an acetabular portal incision, may be on one side of the main incision and may be significantly less than one half inch (½") in length. The incision 14 may be a femoral incision, may be on the other side of the main incision 12 from the acetabular incision 16 and may also be significantly less than one half inch (½") in length. The portal incisions 14 and 16 may be of the same approximate length.

Figure 2:
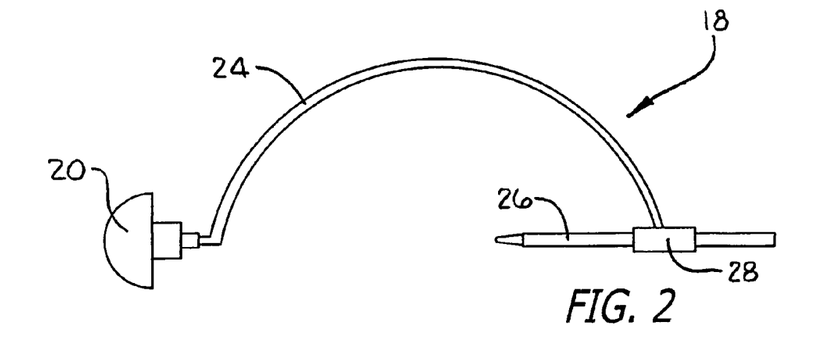
FIG. 2 is a side elevational view of a tool used by a surgeon to determine the positioning of the portal incisions in the patient's hip after the formation of the main incision in the patient's hip.

A tool generally indicated at 18 is shown in FIG. 2. The tool 18 may illustratively be used to locate the position of the portal incision 16. The tool 18 includes a positioning member 20 which may preferably have a hemispherical configuration to fit in an acetabulum 22 (FIG. 4) when the position of the acetabular portal incision 16 is being determined. A looped extension portion 24 extends from the positioning member 20. The portion 24 is preferably looped to extend through the main incision 12 to a position external to the patient's hip 10 and then to extend to a position approximating the position of the acetabular portal incision 16. It will be appreciated that the looped portion 24 may have a different configuration than that shown in FIG. 2 provided that the right end in FIG. 2 has a position corresponding substantially to that shown in FIG. 2. A marker member 26 such as a stylus attached to the looped portion at the right end of the looped portion 24 in FIG. 2. The marker member 26 is retained by a holder 28. As will be seen, the holder 28 and the marker member 26 have a substantially identical axial relationship with the positioning member 20.

Figure 3:
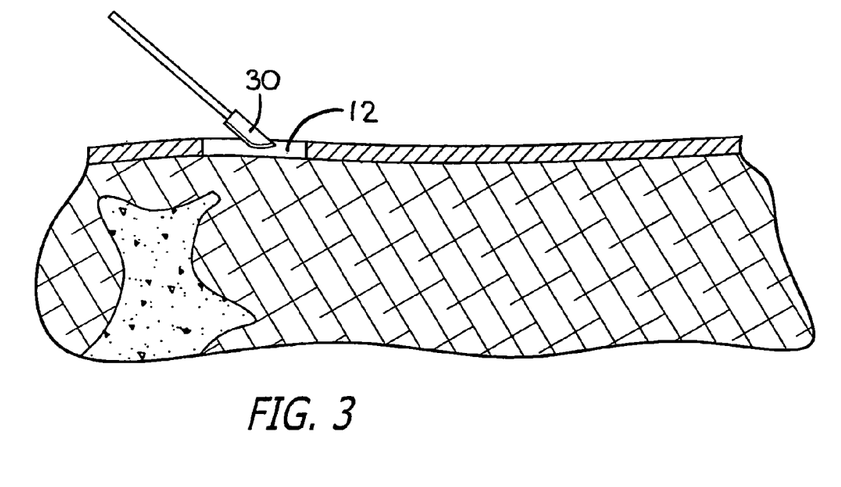
FIG. 3 is an enlarged fragmentary sectional view of a patient's hip and shows the formation of the main incision in the patient's hip.
Figures 4, 5:
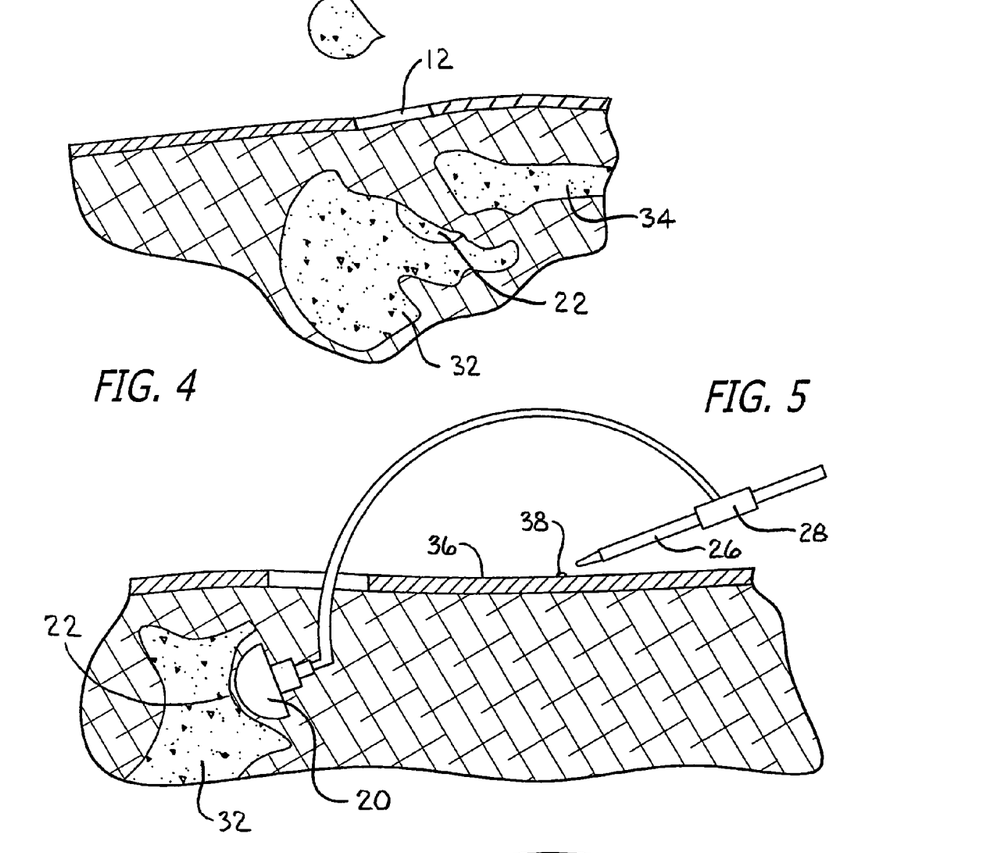
FIG. 4 is an enlarged fragmentary sectional view similar to that shown in FIG. 3 and shows the approximate positioning of the main incision in relation to a hip bone and a femur in the patient.
FIG. 5 is an enlarged fragmentary sectional view similar to that shown in FIG. 4 and shows the positioning of the tool of FIG. 2 in the patient's hip to determine the position of the portal incision for providing an acetabular shaping of the hip bone.

A first step in the performance of applicant's method is shown in FIG. 3. In this step, a cutter 30 is used to provide the main incision 12. This incision is preferably made anterior to, directly over or posterior to the greater trochanter. It will accordingly be appreciated that the positioning of the main incision 12 is somewhat discretionary. FIG. 4 is a somewhat schematic view showing the approximate positioning of the main incision 12 relative to the positioning of the patient's hip bone 32 and femur 34.

Figure 6:
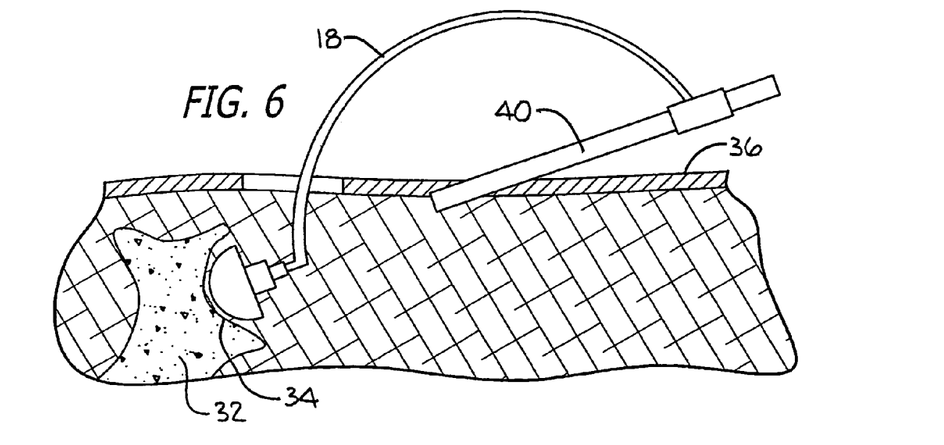
FIG. 6 is an enlarged fragmentary sectional view similar to that shown in FIG. 5 and shows partial insertion of a cannula into the patient's hip through the portal incision to provide for an acetabular shaping in the patient's hip.

FIG. 5 shows the hip bone 32 and the acetabulum 22 in the hip bone. FIG. 5 also shows the disposition of the tool 18 with the positioning member 20 in the acetabulum 22. In this disposition, the marker member 26 abuts the patient's skin 36 in the region of the patient's hip and causes a mark 38 to be produced on the patient's skin. This mark indicates the position to be provided for the acetabular portal incision 16. FIG. 6 illustrates the positioning of a cannula 40 so that it extends through the acetabular incision 16 at the mark 38 in the direction toward the axis of the positioning member 20.

Figure 7:
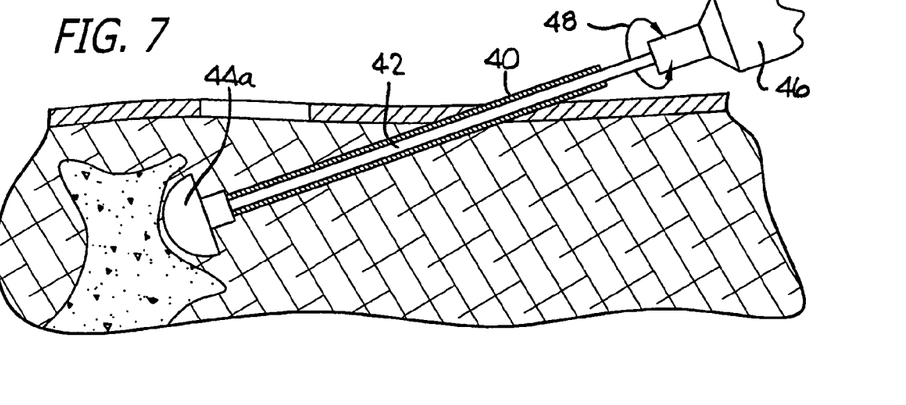
FIG. 7 is a fragmentary sectional view similar to that shown in FIGS. 5 and 6 and shows the positioning of a reamer through the cannula and the operation of the reamer to form the acetabulum in the patient's hip bone.
Figure 8:
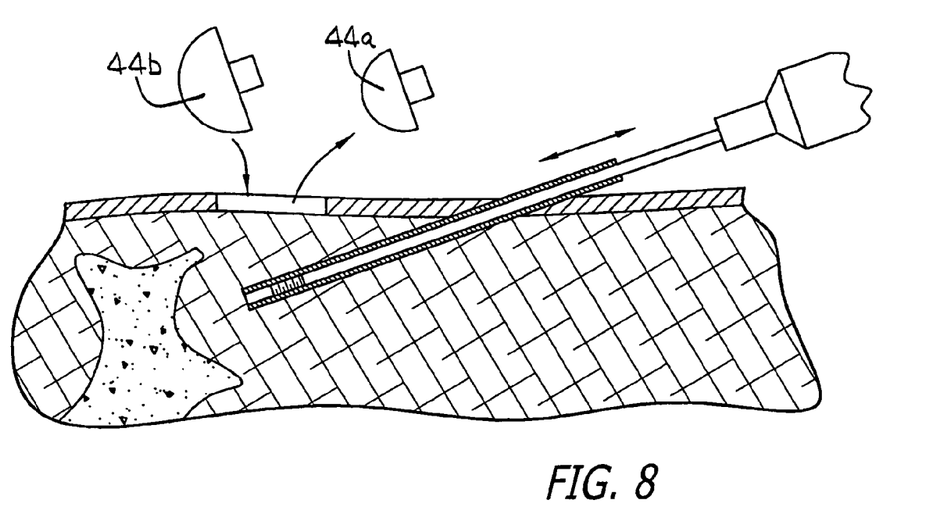
FIG. 8 is an enlarged fragmentary sectional view similar to that shown in FIGS. 5–8 and schematically shows the use of reamers of progressively increased size to shape the acetabulum in the patient's hip.
Figure 9:
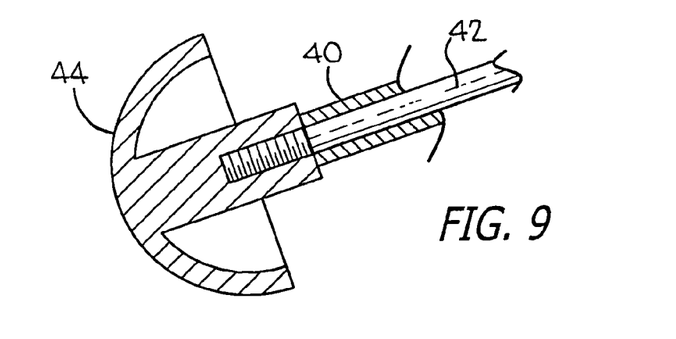
FIG. 9 is an enlarged fragmentary sectional view of one of the reamers shown in FIGS. 5–8.
Figure 10:
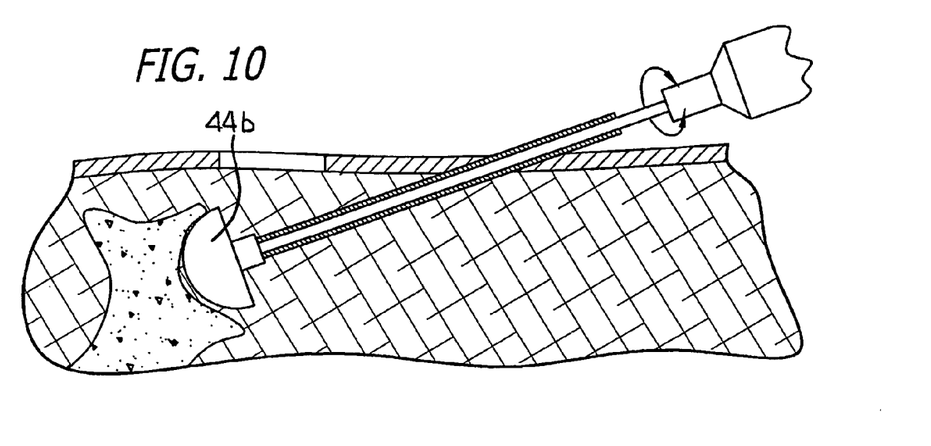
FIG. 10 is an enlarged fragmentary sectional view similar to that shown in FIG. 7 and shows a reamer which is large in comparison to the reamer shown in FIG. 7.
Figure 11:
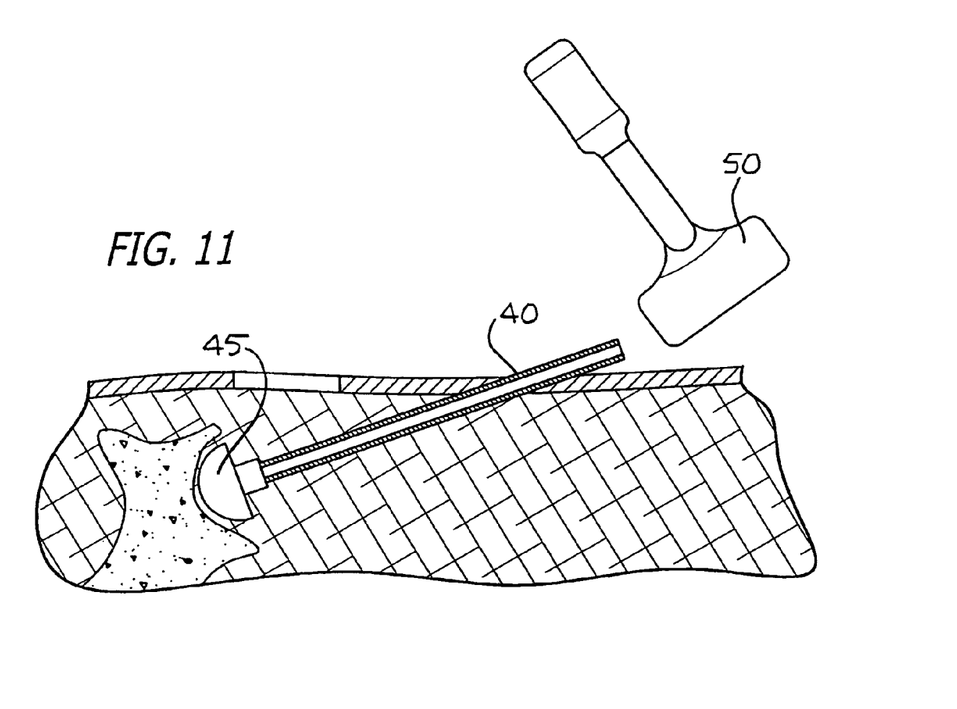
FIG. 11 is a fragmentary sectional view similar to that shown in FIGS. 5 and 6 and shows the insertion of an approximately hemispherical acetabular component into the acetabulum of the patient's hip to provide the pivotable relationship between the femoral ball and the acetabulum in the patient's hip bone.

FIG. 7 shows a shaft 42 extending through the cannula 40 and coupled to a reamer 44 which is disposed in the acetabulum 22. A motor 46 drives the shaft in one rotary direction to operate the reamer 44. The rotary movement of the shaft 42 is indicated at 48. As will be appreciated, the acetabulum 22 is sequentially reamed by reamers 44 of progressively increasing size. This is illustrated at 44a in FIG. 7 and at 44a and 44b in FIG. 8. It may also be seen by comparing the size of the reamers 44a and 44b respectively in FIGS. 7 and 10 and also in FIG. 8. When the acetabulum 22 has the desired shape, size and smoothness, a hemispherical shell (acetabular component or a trial component) 45 (FIG. 11) is introduced into the acetabulum 22 to provide a pivotal relationship with the femoral head. This may be accomplished by applying a mallet 50 to the shaft extending thru the cannula 40 as illustrated schematically at 50 in FIG. 11.

Figure 12:
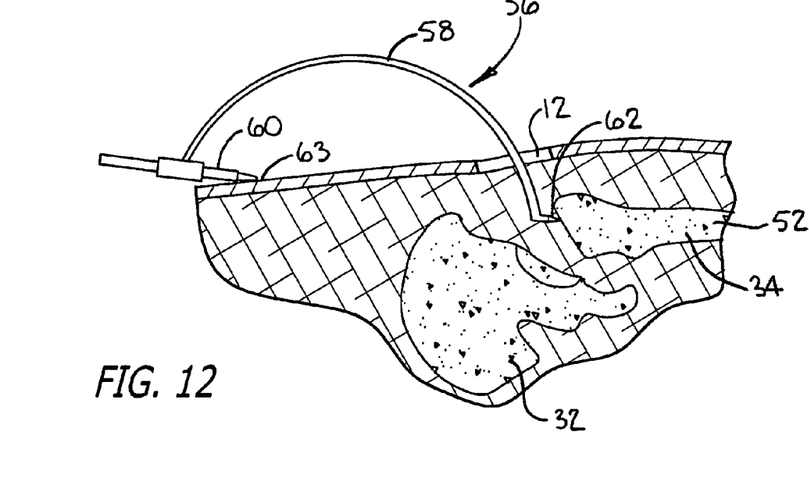
FIG. 12 is an enlarged fragmentary sectional view similar to that shown in FIG. 4 and shows the positioning relative to a femoral stem of a tool similar to that shown in FIG. 2 to determine the positioning of the portal for the femoral incision for obtaining the disposition of a femoral stem in a cavity in the patient's femur.
Figure 13:
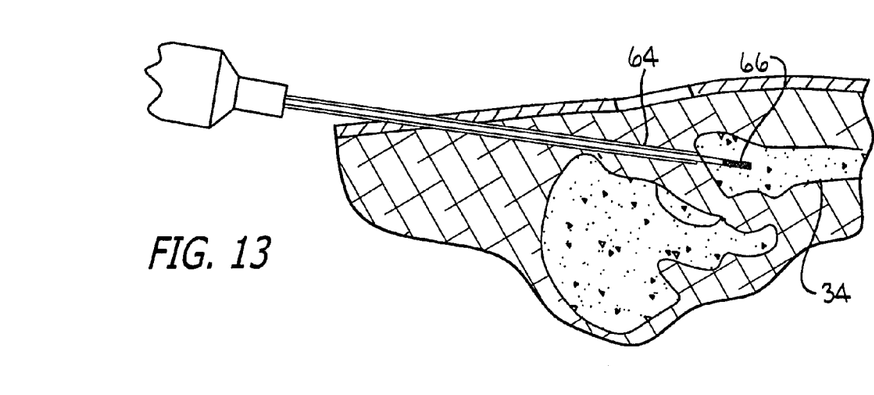
FIG. 13 is an enlarged fragmentary sectional view similar to that shown in FIG. 12 and shows the positioning of a cannula through the portal incision and the positioning of a rasp through the cannula to provide for the smoothing of the walls of the femur cavity.

FIGS. 12–15 relate to the formation of the femoral portal incision 14 and the use of this incision in connection with the disposition of the femoral stem 52 in a cavity 54 (FIG. 15) in the femur 34. As shown in FIG. 12, a tool generally indicated at 56 is provided to determine the position of the femoral portal incision 14. The tool 56 is similar in a number of respects to the tool 18. For example, the tool 56 may include an extension portion 58 and a marker member 60 respectively corresponding in configuration to the extension portion 24 and the marker member 26 in FIG. 2. The dimensions of the extension portion 58 may be different from those of the extension portion 24. The tool 56 may also be provided with a drive member 62 at the end opposite the marker member 60. The drive member 62 may have a finger configuration. The marker member 60 and the drive member 62 preferably are disposed on the same axis. When the drive member 62 is inserted into the main incision 12 and is disposed against the femoral stem 52, the marker member 60 makes a mark 63 a long scalpel blade may be passed thru this portal locator sleeve to indicate the position of the femoral portal incision 14 as shown in FIG. 12. A relatively long scalpel blade may then be passed through this portal locator sleeve.

Figure 14:
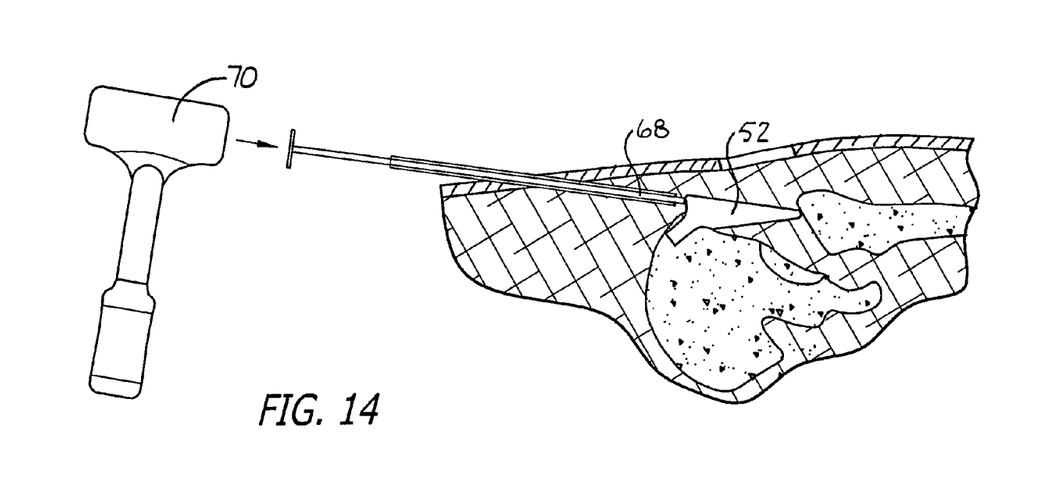
FIG. 14 is an enlarged fragmentary sectional view similar to that shown in FIG. 13 and shows how the femoral stem becomes disposed in the femur cavity.
Figure 15:
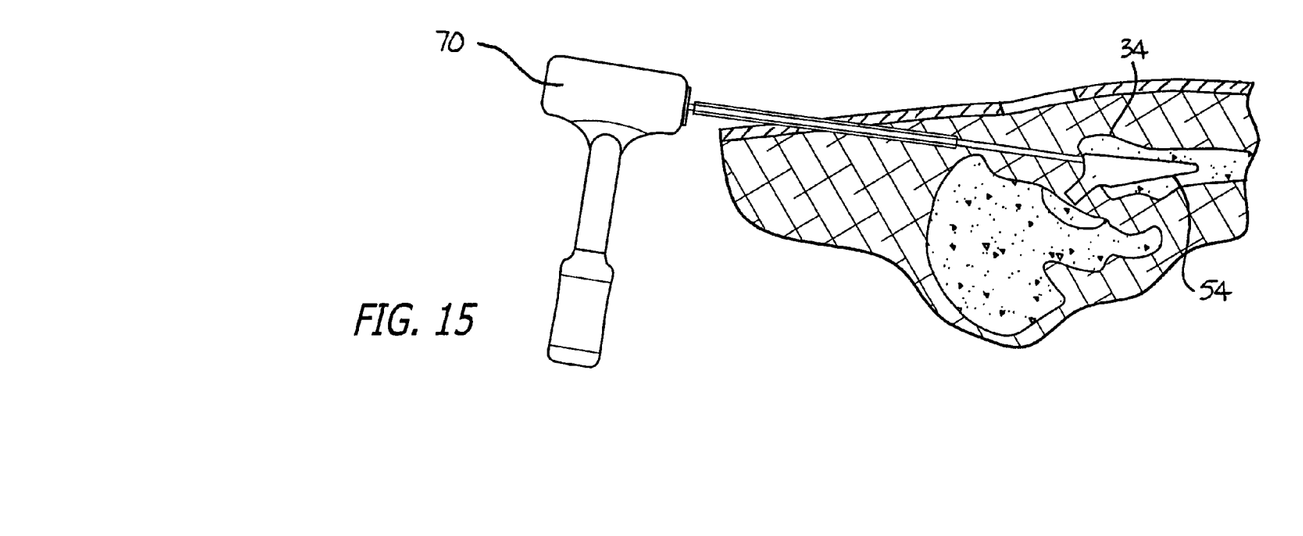
FIG. 15 is an enlarged fragmentary sectional view similar to that shown in FIGS. 13 and 14 and shows the proper disposition of the femoral stem in the femur cavity.

A cannula 64 (FIG. 13) is then inserted through the femoral portal incision 14 to a position adjacent the femoral stem 32. If soft tissues permit, a cannula need not always be used. A rasp 66 or, a reamer, a drill or a tamp is passed through the cannula 64 into the cavity 54 in the femur 34 and is operated to prepare the walls of the cavity to receive the femur. In the claims, the term "rasp" is intended to include a reamer, drill or tamp or other suitable component. The rasp 66, or, a reamer, a drill or a tamp is then withdrawn from the cannula 64 and a drive member 68 (FIG. 14) is inserted through the cannula to abut the femoral stem. This is shown in FIG. 14. A mallet 70 in FIG. 15 is then applied against the drive member 68 to move the femoral stem 52 into the cavity 54 in the femur 34. This is shown in FIG. 15.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. In a method of providing a hip replacement in a patient, the steps of
providing a first incision of a limited length,
determining the position of a femoral portal incision,
making the femoral portal incision at the determined position, and
providing a positioning of an instrument in the hip through the femoral portal incision to facilitate the hip replacement,
wherein the femoral portal incision is provided through the femoral portal position to provide for the insertion of the instrument into the hip for positioning a femoral stem in a femur cavity,
wherein a cannula is disposed in the hip through the femoral portal incision to provide for a positioning of the femoral stem in a cavity in the femur, and
wherein a driver is disposed through the cannula to provide for the positioning and final seating of the femoral stem in the cavity in the femur, and wherein the femoral stem is inserted into the hip through the first incision.

2. In a method of claim 1, further comprising the steps of determining the position of a acetabular portal incision,
making the acetabular portal incision at the determined position, and
providing a positioning of an instrument in the hip through the portal incision to facilitate the hip replacement,
wherein the incision is provided through the acetabular portal position to provide for the preparation of the acetabulum, and
wherein a cannula is disposed through the acetabular portal incision to provide for the formation of the acetabulum.

3. In a method as set forth in claim 2 wherein
a shaft is disposed in the cannula and wherein a reamer is disposed in the acetabulum and the shaft is coupled to the reamer to provide for an operation of the reamer in shaping the acetabulum.

4. In a method as set forth in claim 3 wherein
reamers of progressive size are disposed in the acetabulum and the shaft is coupled to the reamer in the acetabulum and the reamer is rotated to shape and size the acetabulum.

5. In a method as set forth in claim 2 wherein
the first incision is the main incision and wherein
the femoral portal incision is disposed on one side of the main incision and wherein
the acetabular portal incision is disposed on the other side of the main incision.

6. In a method as set forth in claim 1 wherein
a rasp is disposed in the cannula to smooth the walls of the femur cavity before the femoral stem is driven into the femoral cavity.

7. In a method of providing a hip replacement in a patient, the steps of
providing a first incision of a limited length in the patient's hip,
providing a portal incision in the patients hip at a particular disposition displaced from the main incision, the portal incision having a length of about ½ inch or less,
inserting a cannula into the patient's hip through the portal incision to a position providing for an act by a surgeon to facilitate the hip replacement in the patient, and
disposing a tool through the cannula to the position providing for the act by the surgeon to facilitate the hip replacement in the patient,
wherein the locus for the portal incision is determined to provide for the positioning of the femoral stem in the femur cavity, and
wherein the cannula is extended from the femoral portal incision through the hip to the femoral stem which is positioned relative to the femur cavity to be driven into the femur cavity.

8. In a method as set forth in claim 7 wherein
a member is disposed in abutting relationship with a femoral stem to provide a locus for determining the positioning of the portal incision when the portal incision is a femoral portal incision and wherein
the femoral portal incision is made at the position determined for the femoral portal incision.

9. In a method as set forth in claim 7 further comprising
disposing an acetabular portal marker member in an acetabulum in the patient to provide a locus for determining the positioning of an acetabular portal incision,
wherein the locus for the portal incision is determined to provide for the shaping and sizing of the acetabulum in the hip bone, and
making an acetabular portal incision at the determined position of the acetabular portal incision.

10. In a method as set forth in claim 9 wherein
a cannula is disposed to extend from the acetabular portal incision into the hip to the position of the acetabulum in the hip bone.

11. In a method as set forth in claim 10 wherein
a reamer is disposed at the position of the acetabulum in the hip bone and wherein
a rotary drive member is disposed in the cannula and is coupled to the reamer to obtain, when operated, a shaping of the acetabulum.

12. In a method as set forth in claim 11, the step of
sequentially reaming the acetabulum with reamers of progressive size by coupling the rotary drive member to the reamers of the progressive size and rotating the shaft to rotate the reamers.

13. In a method as set forth in claim 7 wherein
a locus for an acetabular portal incision is determined to provide for the shaping and sizing of the acetabulum in the hip bone.

14. In a method as set forth in claim 13,
the cannula is extended from the acetabular portal incision through the hip to the acetabulum to provide for the shaping and sizing of the acetabulum.

15. In a method as set forth in claim 14 wherein
a rotatable drive member is extended through the cannula and wherein
a reamer is disposed in the acetabulum and wherein
the drive member is coupled to the reamer and is rotated to provide for a reaming of the acetabulum by the reamer.

16. In a method as set forth in claim 15 wherein
progressively sized reamers are disposed in the acetabulum and are coupled to the drive member and are rotated by the drive member to shape and size the acetabulum.

17. In a method as set forth in claim 13 wherein
a hemispherical member is disposed in the acetabulum after the shaping and sizing of the acetabulum to provide for a pivotal relationship between the hemispherical member and the acetabulum.

18. In a method as set forth in claim 7 wherein
a drive member is extended through the cannula to the femoral stem and wherein
forces are imposed against the drive member to drive the femoral stem into the femur cavity.

19. In a method of providing a hip replacement in a patient, the steps of
providing a main incision in a patient,
providing an instrument which is planar and which includes a positioning member at one end and a looped portion extending from the positioning member to a marker member at the other end,
disposing the positioning member in the patient with the looped portion extending from the hip through the main incision to a position outside of the hip and with the marker member pointing toward the patient's skin at the patient's hip from the position outside of the hip; and
marking with the marker member the position on the patient's skin at which the marker member contacts the patient's skin, and
wherein the marked position indicates a portal position at which a femoral incision is to be made through which a member is to be inserted to drive a femoral stem into a cavity in the patient's femur.

20. In a method as set forth in claim 19, the step of
making a portal incision at the marked position at which the marker member contacts the patient's skin.

21. In a method as set forth in claim 19 further comprising
providing an acetabular instrument which is planar and which includes an acetabular positioning member at one end and an acetabular looped portion extending from the acetabular positioning member to a acetabular portal marker member at the other end,
disposing the actabular positioning member in the patient with the acetabular looped portion extending from the hip through the main incision to a position outside of the hip and with the acetabular marker member pointing toward the patient's skin at the patient's hip from the position outside of the hip,
marking with the acetabular marker member the position on the patient's skin at which the acetabular marker member contacts the patient's skin, and wherein
the marked position indicates an acetabular portal position at which an acetabular portal incision is to be made through which a driver for an acetabular reamer is to be inserted to form the acetabulum in the patient's hip bone.

22. In a method as set forth in claim 21 further comprising
making an acetabular portal incision at the marked acetabular portal postion,
inserting a driver for an acetabular reamer into the patient's hip through the acetabular portal incision,
inserting an acetabular reamer into the patient's hip through the main incision and coupling the acetabular reamer to the driver to provide a reaming action on the acetabulum in accordance with the rotation of the driver.

23. In a method as set forth in claim 21 wherein
the acetabular positioning member has a substantially hemispherical shape and wherein the hemispherical member is disposed in the patient's acetabulum when the instrument is used to mark the portal position.

24. In a method as set forth in claim 19 wherein
the positioning member constitutes a drive member and wherein the drive member is disposed in abutting relationship to the femoral stem when the instrument is used to mark the portal position.

25. In a method as set forth in claim 19, the step of
using the main incision and the portal incision to provide for the positioning of a drive member for facilitating the hip replacement.

26. In a method as set forth in claim 25 wherein
the portal incision is a femoral incision and wherein the main incision and the femoral portal incision are used to provide for the positioning of a drive member to drive the femoral stem into a cavity in the femur for facilitating the hip replacement.

27. In a method of providing a hip replacement in a patient, the steps of:
providing a first incision of limited length,
determining the position of an acetabular portal incision disposed on a first side of the first incision and displaced from the first incision, and
determining the position of a femoral portal incision disposed on a second side of the first incision opposite the first side of the first incision and displaced from the first incision.

28. In a method as set forth in claim 27 wherein
the first incision has a length as short as approximately one inch (1") and each of the acetabular and portal incisions is less than one-half inch (½") long.

29. In a method as set forth in claim 27 wherein
the first incision extends in a particular direction and wherein
the acetabular portal incision is displaced from the first incision in the particular direction on a first side of the first incision and wherein
the femoral incision is displaced from the first incision in the particular direction on a second side of the first incision opposite the first side.

30. In a method as set forth in claim 29 wherein
the first incision is substantially linear and wherein the acetabular and femoral portal incisions are on extensions substantially of the line defining the first incision.

31. In a method as set forth in claim 27 wherein
the acetabulum is shaped by extending at least one reamer through the acetabular portal incision to the acetabulum and operating the at least one reamer.

32. In a method as set forth in claim 31 wherein
the first incision is substantially linear and wherein the acetabular and femoral hip portal incisions are on extensions substantially of the line defining the first incision and wherein
the acetabulum is shaped by extending at least one reamer through the acetabular portal incision to the acetabulum and operating the at least one reamer and wherein
the femoral stem is positioned in the femoral portal incision by imposing a force against a drive member positioned in the femoral portal incision.

33. In a method as set forth in claim 32 wherein
the first incision has a length as short a approximately one inch (1") and each of the acetabular and portal incisions is less than one-half inch (½") long.

34. In a method as set forth in claim 27 wherein
the femoral stem is positioned in the femoral portal incision by imposing a force against a drive member positioned in the femoral portal incision.

35. In a method of providing a hip replacement in a patient, the steps of:
providing a first incision of a limited length,
using the first incision as a reference to determine a position for making a first marking on the patient's skin at a position defining a selective one of an acetabular portal and a femoral portal, and using the first incision as a reference to determine a position for making a second marking on the patient's skin of a position defining the other one of the acetabular portal and the femoral portal, wherein a second incision is made in the patient's body at the position of the first marking and wherein a third incision is made in the patient's body at the position of the second marking.

36. In a method as set forth in claim 35 wherein a first tool is provided through the second incision to act upon the selective one of the acetabulum and femur and wherein a second tool is provided through the third incision to act upon the other one of the acetabulum and femur.

37. In a method as set forth in claim 35 wherein the first incision has a length as short as approximately one inch (1") and each of the second and third incisions is less than approximately a half inch (½") long.

38. In a method as set forth in claim 35 wherein a first tool is provided through the second incision to act upon the selective one of the acetabulum and femur and wherein a second tool is provided through the third incision to act upon the other one of the acetabulum and femur and wherein the first incision has a length as short as approximately one inch (1") and each of the second and third incisions is approximately a half inch (½") long.

39. In a method of providing a hip replacement in a patient, the steps of:

providing a first incision of a length of less than approximately one inch (1"), using the first incision as a reference to provide a second incision displaced from the first incision and having a length less than approximately one-half inch (½") at a position providing for the insertion of a first tool through the second incision to the acetabulum to shape the acetabulum, and using the first incision as a reference to provide a third incision displaced from the first and second incisions and having a length less than approximately one-half inch (½") at a position providing for the insertion of a second tool through the third incision to the femur to drive a femoral stem into a cavity in the femur.

40. In a method as set forth in claim 39 wherein the first incision is disposed between the second and third incisions.

41. In a method as set forth in claim 40 wherein the first incision is substantially linear and wherein the second and third incisions are disposed respectively at second and third portions corresponding to positions of linear extensions of the first incision and wherein the first incision is anterior to, directly over or posterior to the greater trochanter.

42. In a method as set forth in claim 39 wherein the first incision is substantially linear and wherein the second and third incisions are disposed respectively at second and third portions corresponding to positions of linear extensions of the first incision.

43. In a method as set forth in claim 39 wherein the first incision is anterior to, directly over or posterior to the greater trochanter.

* * * * *